(12) United States Patent
Scheer

(10) Patent No.: US 8,161,902 B2
(45) Date of Patent: Apr. 24, 2012

(54) MULTI-PURPOSE HOLDING DEVICE

(76) Inventor: Ingo Scheer, La Jolla, CA (US)

( * ) Notice: Subject to any disclaimer, the term of this patent is extended or adjusted under 35 U.S.C. 154(b) by 817 days.

(21) Appl. No.: 12/279,839

(22) PCT Filed: Feb. 26, 2007

(86) PCT No.: PCT/US2007/005122
§ 371 (c)(1),
(2), (4) Date: Aug. 18, 2008

(87) PCT Pub. No.: WO2007/100838
PCT Pub. Date: Sep. 7, 2007

(65) Prior Publication Data
US 2010/0227045 A1 Sep. 9, 2010

Related U.S. Application Data

(60) Provisional application No. 60/776,522, filed on Feb. 24, 2006.

(51) Int. Cl.
*B05B 13/04* (2006.01)

(52) U.S. Cl. ........ 118/320; 118/500; 118/504; 118/505; 427/2.24; 427/240

(58) Field of Classification Search .................. 118/500, 118/504, 505, 320; 427/2.24, 240
See application file for complete search history.

(56) References Cited

U.S. PATENT DOCUMENTS

| | | | |
|---|---|---|---|
| 6,565,659 B1 * | 5/2003 | Pacetti et al. | 118/500 |
| 7,404,979 B1 * | 7/2008 | Pacetti | 427/2.24 |
| 7,416,609 B1 * | 8/2008 | Madriaga et al. | 118/500 |

* cited by examiner

*Primary Examiner* — Dah-Wei Yuan
*Assistant Examiner* — Andrew Bowman

(57) ABSTRACT

This invention relates to a multi-purpose holding device to handle, support and rotate one or more hollow cylindrical objects. The holding device consists of a rigid frame and support members for precise alignment and rotation of one or more objects within the frame structure. A method is also provided to reproducibly support, rotate and inspect the hollow cylindrical objects.

20 Claims, 10 Drawing Sheets

C-C

_US 8,161,902 B2_

MULTI-PURPOSE HOLDING DEVICE

CROSS-REFERENCE TO RELATED APPLICATIONS

This Application relates to and claims priority from commonly owned U.S. Provisional Patent Application Ser. No. 60/776522, filed on Feb. 24, 2006 and U.S. patent application Ser. No. 11/431,366, filed on May 9, 2006.

FEDERALLY SPONSORED RESEARCH

Not Applicable

SEQUENCE LISTING OR PROGRAM

Not Applicable

TECHNICAL FIELD

This invention relates to a holding device and a method of coating hollow cylindrical objects using the device. More specifically, the present invention provides a holding device and a method of reproducibly and securely supporting and rotating one or more hollow cylindrical objects, such as stents, during a coating process while minimizing runout of the hollow cylindrical object during rotation, and surface contact between the hollow cylindrical object and the holding device.

BACKGROUND

Coatings are often applied to medical appliances, such as pacemakers, vascular grafts, stents, and heart valves, to have desired effects and increase their effectiveness. These coatings may deliver a therapeutic agent or drug to the lumen that reduces smooth muscle tissue proliferation or restenosis. Furthermore, medical devices may be coated to provide beneficial surface properties, achieving enhanced biocompatibility and to improve surface properties such as lubriciousness. Balloon delivery systems, stent grafts and expandable stents are specific examples of medical appliances or implants that may be coated and inserted within the body. Stents such as described in U.S. Pat. No. 4,733,665, are tiny, expandable mesh tubes supporting the inner walls of a lumen used to restore adequate blood flow to the heart and other organs.

Conventionally, coatings are applied to the stent in a number of ways including, though not limited to, dip coating, spin coating or spray coating. Spray coating processes generally require an apparatus to securely hold and rotate the flexible, tiny stent structure during the coating operation to allow a reproducible and homogeneous coating application on the whole surface.

However, holding devices known from the prior art have several drawbacks which may result in low volume production of medical devices, damage to the fragile stent structure, inhomogeneous coatings, uncoated areas, coating accumulations, and the like. Coating accumulations, such as shown in FIG. 13, can lead to severe damages of the coating due to a possible loss of the coating during loading, transportation, and/or deployment of the stent. Coating defects, such as uncoated areas and coating thickness variations on the stent surface may compromise the implant's effectiveness due to potential complications arising from an inhomogeneous distribution of the therapeutic agent at the target site.

Stent holding devices, as described in U.S. Pat. No. 6,605,154, comprising a mandrel passing all the way through the inner hollow body of the stent to support the stent via support members, which partially penetrate into the opposing sides of the hollow body of the stent by incrementally moving at least one support member closer to the other, can have several disadvantages.

When using such stent holding devices there may be a risk of coating defects at the ends of the stent due to the design of the support elements. The clamping force can vary from stent to stent, which may lead to sagging or buckling of the stent. Mandrels having a small diameter and a comparatively long length of approximately 40-80 mm may easily bend resulting in a runout of the stent. In most cases the run out of the mandrel is several mm which may effect the coating weight consistency. Moreover stent holding devices, as described in U.S. Pat. No. 6,572,644, comprising members projecting out of a body to contact the stent may not center and secure the stent sufficiently.

Runout, sagging and buckling of the stent may cause an inhomogeneous coating thickness, coating defects on the stent surface and coating weight deviations. Coating consistency may vary from stent to stent depending on runout and positioning accuracy of the support members.

In addition, coating defects including uncoated areas may arise when stent holding devices are used having a structure which interferes with the spray plume as described in WO Pat. No. 2004/008995.

Damage of the coating may also occur after completion of the coating process during handling and inspection. Inspection of medical devices generally requires dismounting the stent from the holding device being used during the coating process in order to mount the stent to an inspection fixture that typically contacts the outer surface of the stent.

Finally, stent holding devices known by the prior art are not designed to support and/or coat multiple stents simultaneously or to be used for subsequent inspection of the coated stents.

SUMMARY

There is therefore a need for a device and a coating method which will improve the efficiency, stability and reproducibility of the stent coating process by securing the stent during the coating operation without disturbing the coating process, damaging the medical device and/or coating and by permitting higher volume, low cost production of high quality coated medical devices.

Accordingly, a multi-purpose holding device for handling, securing and rotating one or more medical devices and a method for coating one or more medical devices, such as stents, is provided. The holding device includes a rigid frame structure and interchangeable support members to allow precise alignment of the medical device within the frame structure and minimized runout. To avoid coating defects, the support member do not extend completely through the medical device, provide minimized surface contact with respect to the medical device and do not block the spray plume from uniformly coating the entire stent.

In one embodiment of the present invention, a holding device for handling, securing and rotating at least one stent is provided. The holding device comprises a frame and at least two support members being coupled to the frame and in contact with at least a portion of the stent. The support members have a first position of being engaged with the stent at two opposing sides to securely hold the stent and the support members can be rotated in relation to the frame to rotate the stent. At least one support member has a second position of being disengaged from the stent to unload the stent. In one or more embodiments, the holding device further comprises at least one shaft, which can be rotated in relation to the frame in order to transmit rotary motion to the support members. It may also comprise members to transmit rotary motion between the shaft and the support members. In addition, sleeves may be rotably mounted to the frame so that in the first position the support member is coupled to the sleeve to transmit rotary motion, and in the second position the support member is uncoupled from the sleeve. Each support member may comprises a structure at least partially surrounding the end of the stent and a member, such as a thread or a rod, connecting the surrounding portion of the structure in order to contact the stent. The member may be part of the structure or may be exchangeable, and may include at least one portion with a larger cross-section having a spherical or a cylindrical shape to center the stent. The support member may contact at least partially the inner surface of the stent and the portion of the support member contacting the inner surface of the stent may comprise at least two sides being parallel to the longitudinal axis of the stent. Alternatively, the support member may contact at least partially the inner surface of the stent and the portion of the support member contacting the inner surface of the stent may comprise at least two edges being parallel to the longitudinal axis of the stent.

In a next embodiment, a method is provided for securing and rotating at least one stent using a holding device having a frame and at least two opposing support members being coupled to the frame, which are coaxially arranged and can be rotated in relation to the frame. In a first step, at least one support member is located at a first position in which the distance between the support members is larger than the stent length. In a next step, a stent is positioned between the support members. Then, at least one support member is located at a second predetermined position in which the distance between the support members is smaller than the stent length to reproducibly secure the stent. In another step, rotary motion is transmitted to the support member to rotate the stent in relation to the frame. In one or more embodiments, a shaft being rotably mounted to the frame is additionally provided and rotary motion is induced in the shaft and transmitted to the support members to rotate the stent in relation to the frame. In a further step, the holding device may be positioned so that the holding device is at least partially in contact with one or more guide members and the holding device may be translated along the guide member. In another step, a coating may be applied to the stent.

In still another embodiment, an apparatus for translating and rotating one or more stents comprises at least one guide member and a detachable holding device having a frame, at least one shaft being rotable in relation to the frame, and at least two support members being rotable in relation to the frame and securing a stent at two opposing ends. The holding device is in contact with at least a portion of the guide member to secure its angular position and can be moved along the guide member to translate the stent, and the stent can be rotated in relation to the holding device by applying rotary motion to at least one of the rotable members being coupled to the frame.

In one or more embodiments, the apparatus may further comprise a spray source to apply a coating to the stent. The apparatus may additionally include at least one motion unit to transmit rotary and linear motion to the holding device in order to rotate and translate the stent. Furthermore, at least one inspection device may also be provided and the holding device can be moved along one or more guide members to position the stent in relation to the inspection device.

In yet another embodiment, a holding device for handling, securing and rotating at least one medical device is provided. The holding device includes a frame and at least one support member contacting at least a portion of the medical device, wherein the support member is coupled to the frame and can be rotated in relation to the frame to rotate the medical device. In one or more embodiments, the holding device may further comprise a shaft being mounted to the frame, which can be rotated in relation to the frame to transmit rotary motion to at least one support member.

DRAWINGS

The accompanying drawings, which are incorporated in and constitute a part of this specification, serve to explain the principles of the invention. The drawings are in simplified form and not to precise scale.

DETAILED DESCRIPTION

Figure 1A:
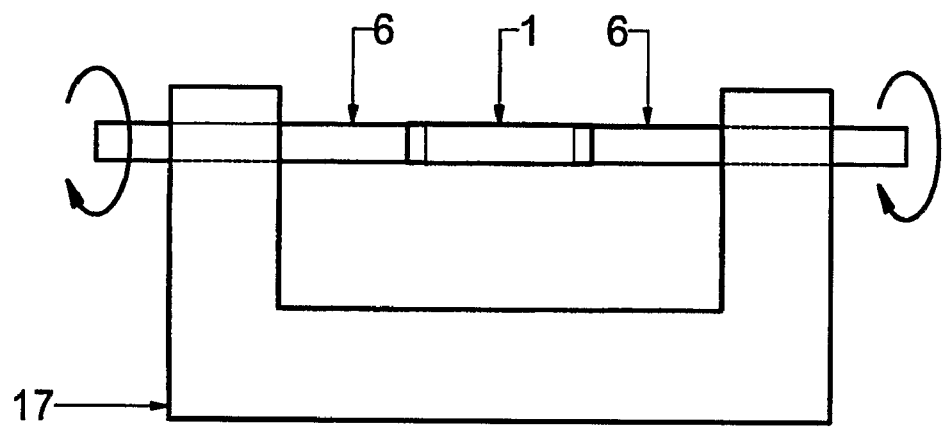
FIG. 1A is a front view showing a holding device to support and to rotate one or more stents.
Figure 1B:
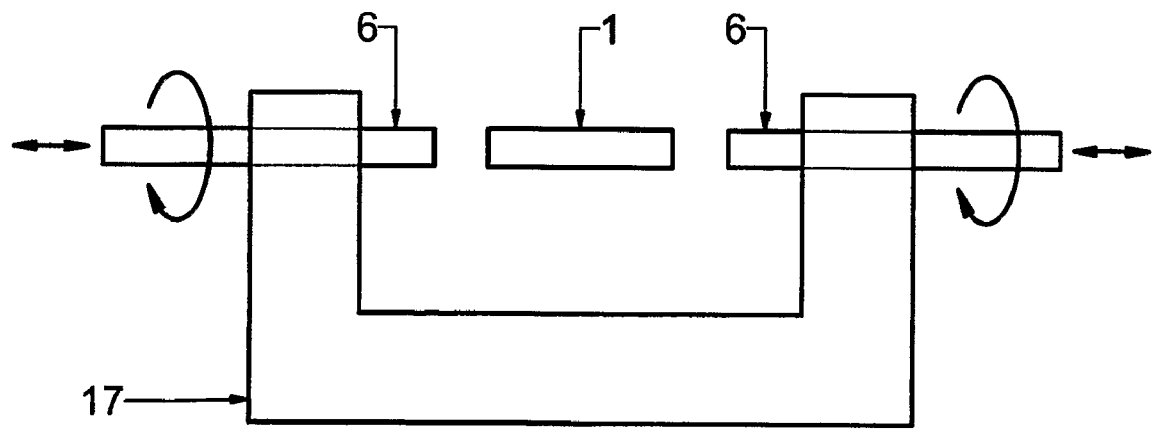
FIG. 1B is a front view showing the holding device with mounted stent.

The following figures illustrate embodiments of a holding device and a method to secure and/or rotate one or more medical devices during various process steps, such as handling and the application and/or inspection of a coating. FIG. 1A and FIG. 1B depict a schematic of an exemplary holding device including a frame 17 and one set of support members 6 being bearing mounted to the frame to securely hold a stent. Referring now to FIG. 1A, stent 1 is positioned between the support members 6, which are engaged with the stent at two opposing sides so that the stent is securely held and can be rotated in relation to the frame (first position). In FIG. 1B the support members are disengaged from the stent to unload the stent by moving at least one support member in axial direction away from the stent (second position). Both support members remain coupled to the frame.

The rigid frame structure of the holding device not only ensures secure handling of the stent, but also precisely coaxially aligns the support members holding the stent at both ends during rotation to prevent run out of the stent. The holding device is designed to secure and rotate multiple stents simultaneously resulting in minimized damage during handling and high volume production of medical devices.

Figure 2:
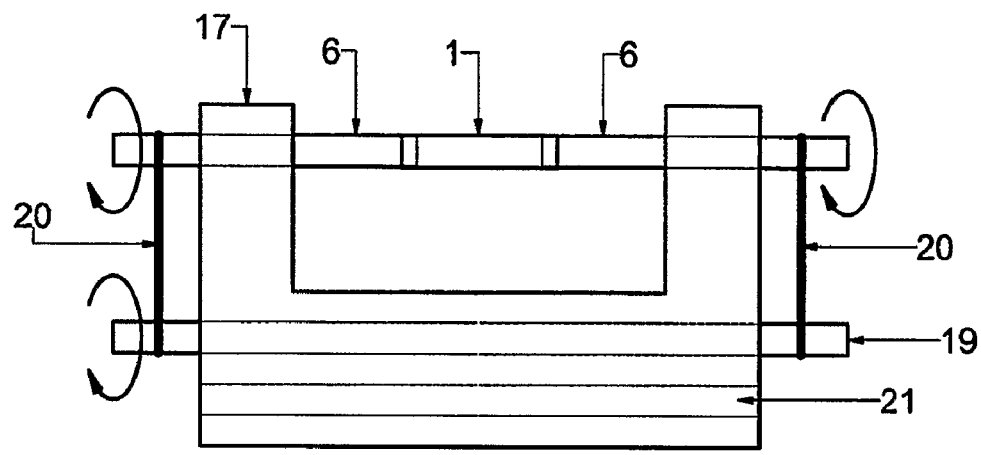
FIG. 2 is a front view showing a holding device to support and to rotate one or more stents including a shaft and a guide section.

To transmit rotational and/or translational motion to the stent, the holding device is preferably coupled to a motion unit comprising one or more motors. FIG. 2 shows a mechanism to transmit rotary motion to the stent. The support members 6 are engaged with the stent 1 at two opposing sides so that the stent is securely held and can be rotated in relation to the frame. To avoid stress due to torsion during rotation of the stent, both support members are preferably driven from either side. The two support members 6 are connected with belts 20 to the shaft 19 and rotary motion is transmitted from one support member 6 or from the shaft 19 via belts to the other support member 6. Alternatively, the shaft and the support member may be equipped with gears and rotary motion is transmitted via gears to the stent. Guide or lock section 21 is provided to secure the angular position of the holding device during rotation of the stent and to prevent revolving of the holding device.

Figure 3:
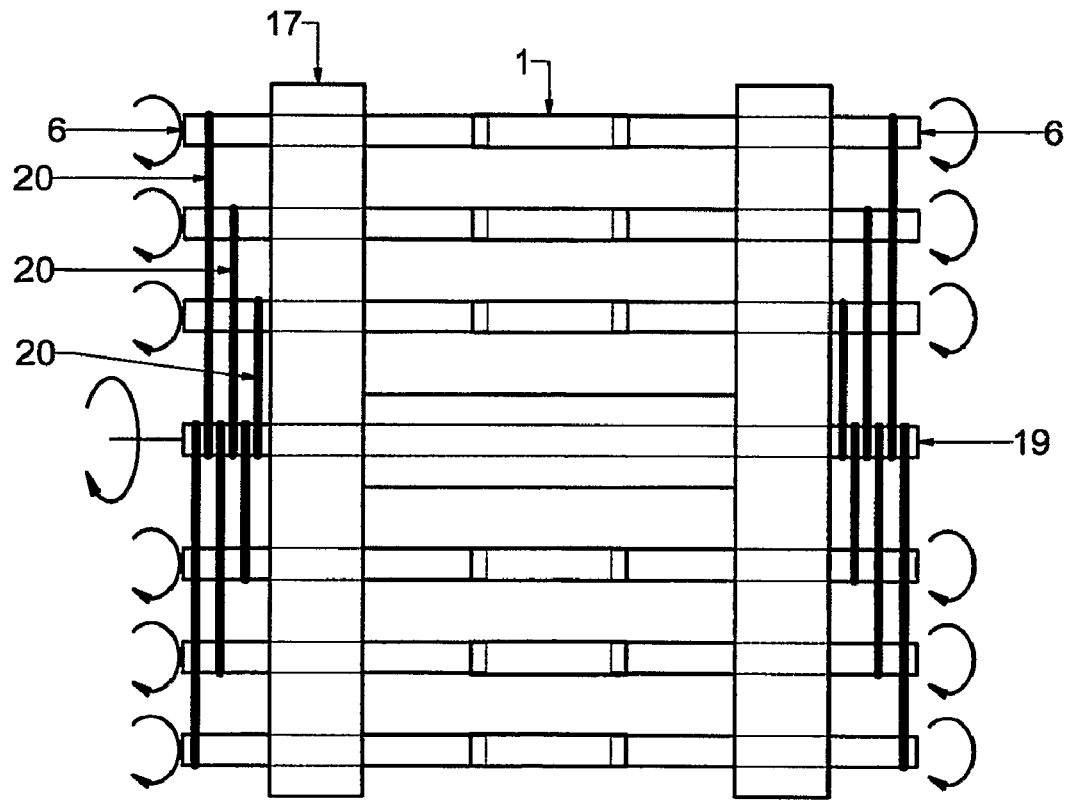
FIG. 3 is a top view showing a holding device to support and to rotate six stents.

The holding device of the present invention is designed to secure and rotate multiple stents simultaneously, as depicted in the schematic representation of FIG. 3. Shaft 19 and six sets of support members 6 being connected to the shaft with belts 20 are rotably mounted to the frame 17. Rotary motion is transmitted from the shaft 19 or from one of the support members 6 to the opposing support member to rotate six stents simultaneously about their longitudinal axis within the frame structure.

The holding device may be further equipped with sleeves, stop members and a coupling to facilitate mounting of the support members, to ensure a reproducible engagement position between the stent and the support members, and to easily engage and disengage the stent.

Figure 4A:
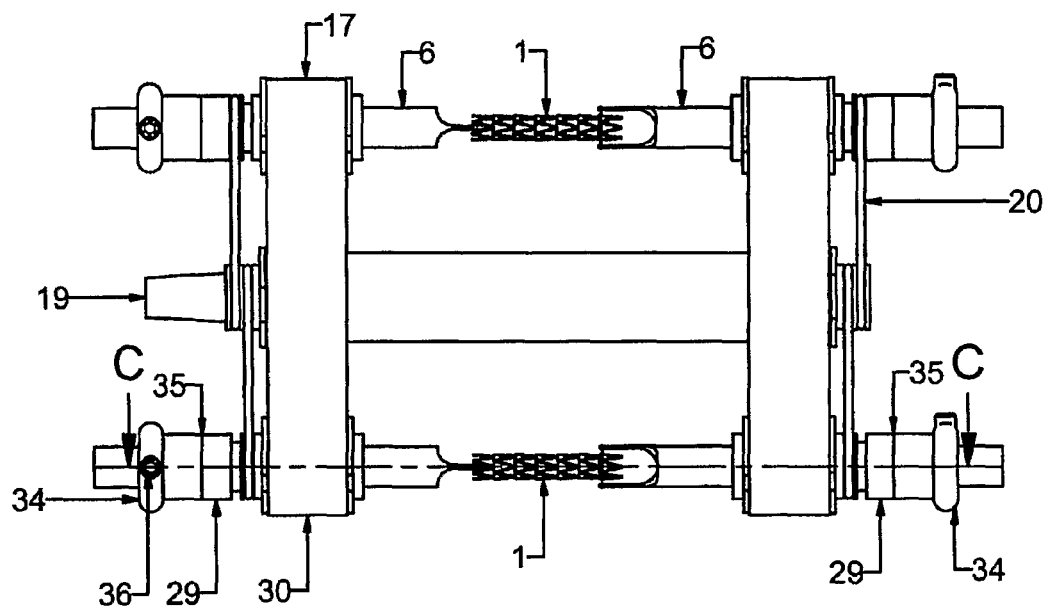
FIG. 4A is a top view of a holding device to support and rotate two stents.
Figure 4B:
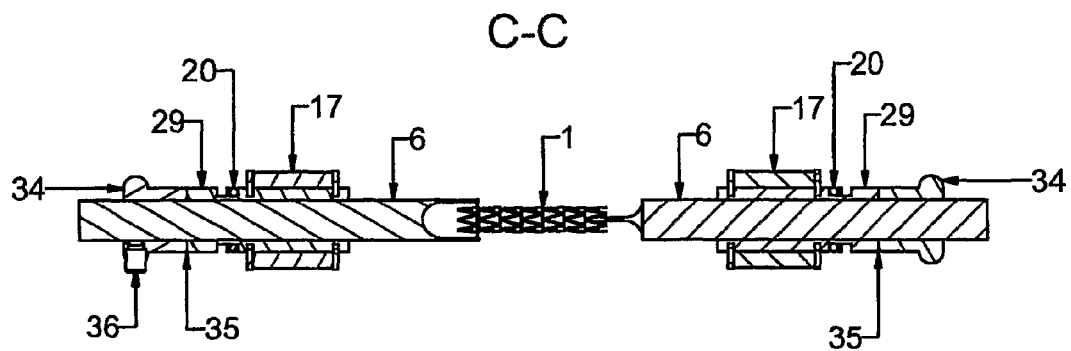
FIG. 4B is a cross-section view of the holding device of FIG. 4A.

With reference to FIG. 4A and FIG. 4B, the sleeves 29 are rotably mounted to the frame and coupled via belts 20 to the shaft 19 to facilitate mounting and to transmit rotary motion to the support members. A magnetic coupling 35 is provided to couple the stop members 34 to the sleeves 29. The stop members 34, which are in contact with the support members 6, define the securing position of the support members 6 in relation to the stent 1, so that the stent can be contacted at a predetermined position. Thus, axial displacement of the support members is prevented and a reproducible positioning of the support members in relation to the stent is ensured.

Figure 5A:
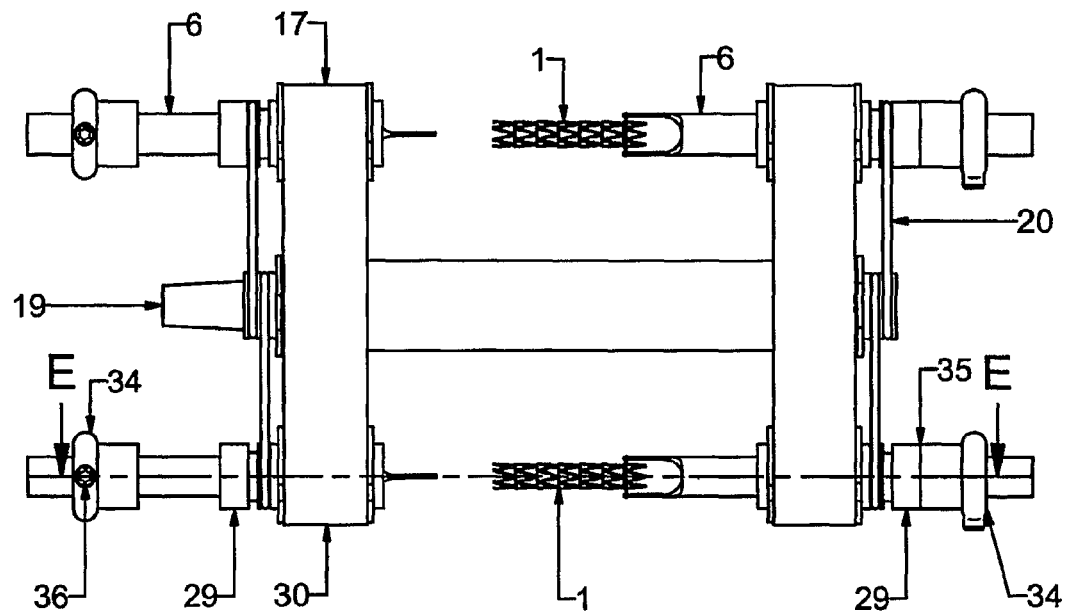
FIG. 5A is a top view of a holding device to support and rotate two stents during unloading.
Figure 5B:
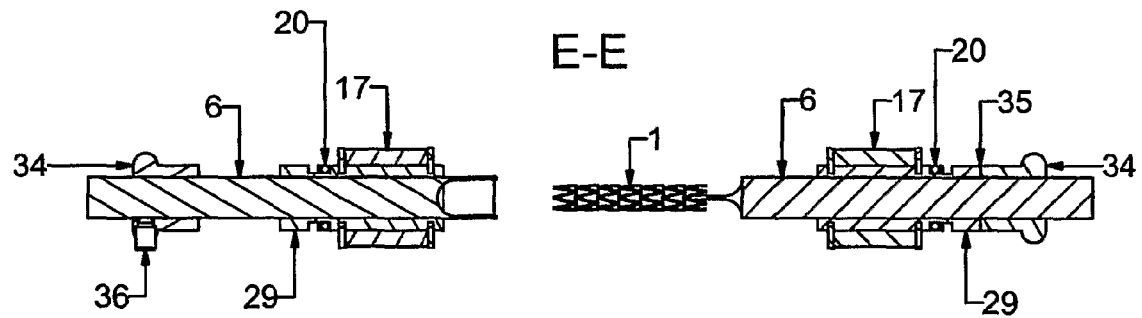
FIG. 5B is an cross-section view of the holding device of FIG. 5A.

In a first position, as illustrated in FIG. 4A and FIG. 4B, the support members are engaged with the stent 1 and the stop members 34 are coupled to the sleeves 29 to secure the stent 1. Rotary motion is transmitted between the shaft 19 and the stent 1 via belts 20, sleeves 29, coupling 35, stop members 34, and support members 6. In a second position, as depicted in FIG. 5A and FIG. 5B, at least one support member 6 is disengaged from the stent 1 to unload the stent. The arrangement comprising support member 6 and stop member 34 is displaced in axial direction to release the stent 1. Alternatively, the position of the support members 6 may be determined by a lock member, such as a pin or a securing ring, which may be detachably coupled to the support members.

The holding device of the present invention can include support members of different types to securely hold stents of various sizes, designs and rigidity. The support members are designed to center the stent so that the longitudinal axis of the stent is coaxial with the rotation axis and to provide a stable connection during transmission of rotary motion. In order to prevent deposition of coating material on the stent holding device, the contact area between the support member and the stent is preferably minimized, namely limited to the edges and/or to a small section within the inner surface near the ends of the stent. At least a portion of the support member may be interchangeable to facilitate cleaning and adaptation to various medical devices and coating setups. FIGS. 6 to 9 illustrate exemplary support members used to secure stents.

Figure 6A:
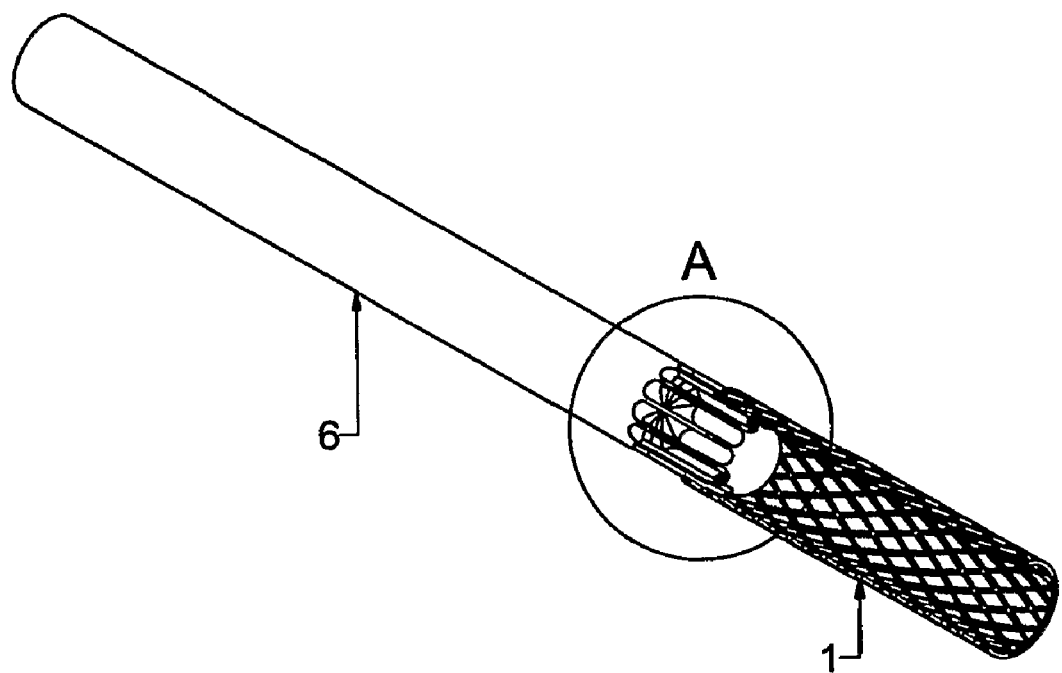
FIG. 6A is an isometric view showing a support member to contact a stent.
Figure 6B:
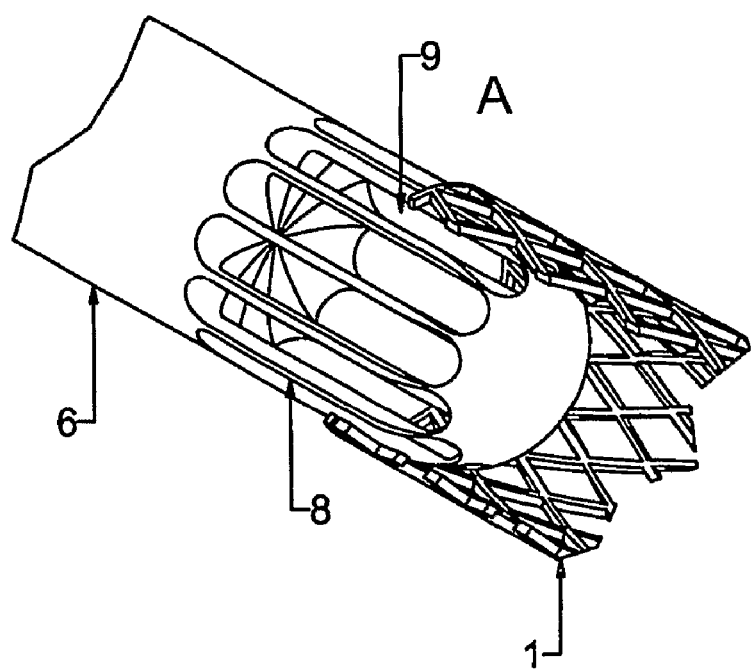
FIG. 6B is an isometric detail view of FIG. 6A.

Referring to FIG. 6A, an exemplary support member with mounted stent is shown. The support member is shown in more detail in FIG. 6B. In order to reduce the contact area between support member 6 and stent 1 while securely holding stent 1, the support member comprises passages 9 at the portion contacting the inner section of the stent. To facilitate stent mounting, the tips of the support members are preferably rounded and can have a hemispherical shape. The portion contacting the inner surface of the stent may be detachably mounted to facilitate cleaning and allow adaptation to various stent sizes. The passages 9 have the shape of slots and are equally distributed on the circumferential surface of the support member. Crosspieces 8 are formed, which comprise the outer surface of the support member 6 and secure the stent by contacting its inner surface. To securely hold the stent, the portion of the support member contacting the inner surface of the stent comprises at least two sides being parallel to the longitudinal axis of the stent. The support members can be constructed from a suitable metallic material, such as stainless steel, titanium, cobalt chromium alloys, or a suitable polymeric material like Polyetheretherketone (PEEK). The passages 9 are preferably manufactured using a micro mill or a micro ECM and may have various shapes. Alternatively, the support members may be made from a folded sheet or be constructed from a hollow profile and may comprise passages.

Figure 7:
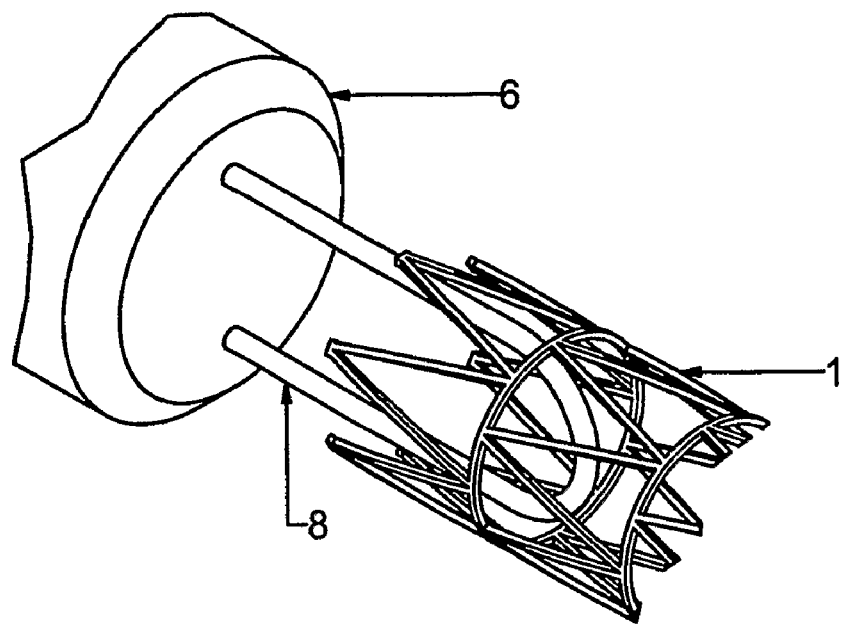
FIG. 7 is an isometric view showing an alternative support member to contact a stent.

To avoid defects on the surface of the stent due to coating residuals that may accumulate on the support member or between support member and stent, it is desirable to further minimize the contact area between stent and support member. FIG. 7 depicts a variation of the support member 6 described before. It comprises a structure 8 contacting the inner surface of the stent 1. The structure, which may be made from a bended wire having a diameter between 0.3 and 0.8 mm, includes two contact sections being located parallel to the longitudinal axis of the stent.

Figure 8:
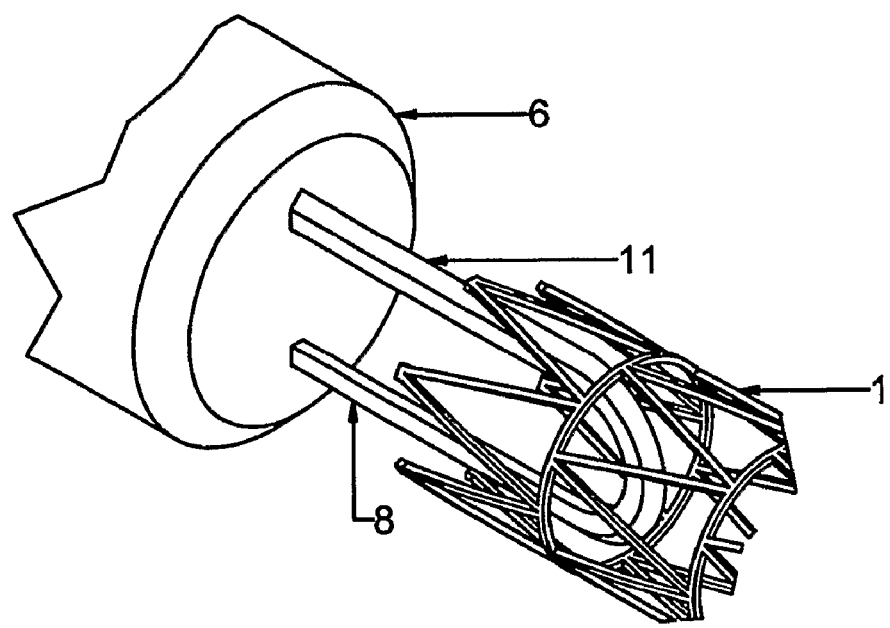
FIG. 8 is an isometric view showing an alternative support member to contact a stent.

Alternatively as shown in FIG. 8, the structure may comprise edge 11 and the inner surface of the stent is in contact with the edge being parallel to the longitudinal axis of the stent.

Figure 9A:
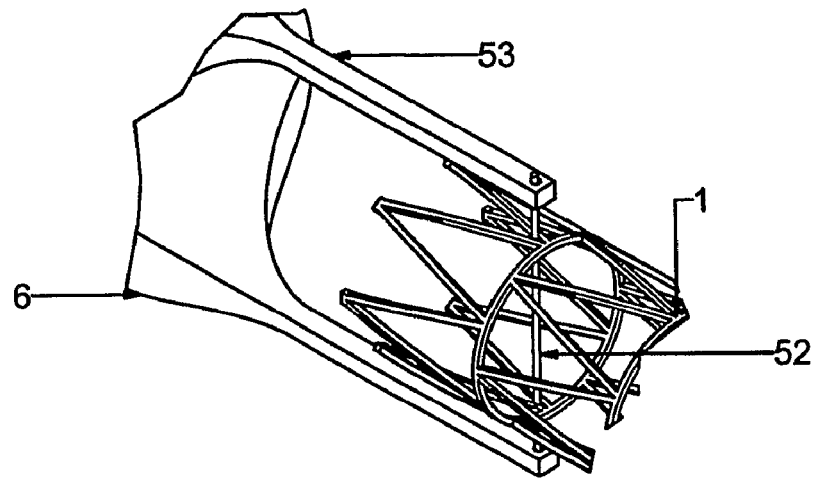
FIG. 9A is an isometric view showing an alternative support member to contact a stent.
Figure 9B:
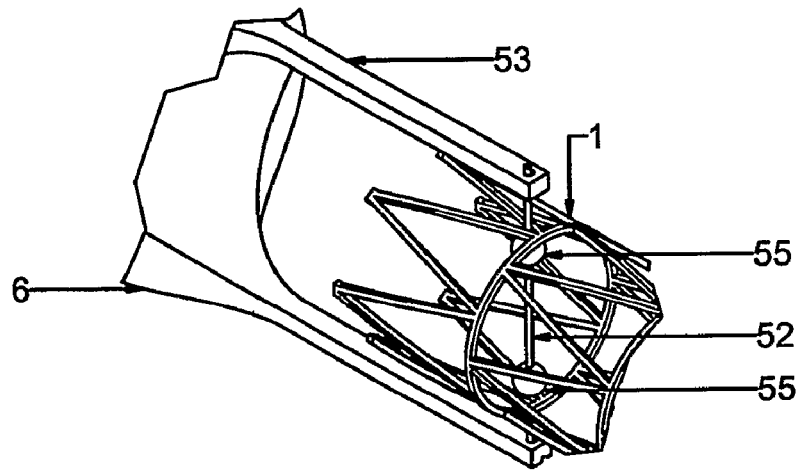
FIG. 9B is an isometric view showing an alternative support member to contact a stent having two centering elements.
Figure 9C:
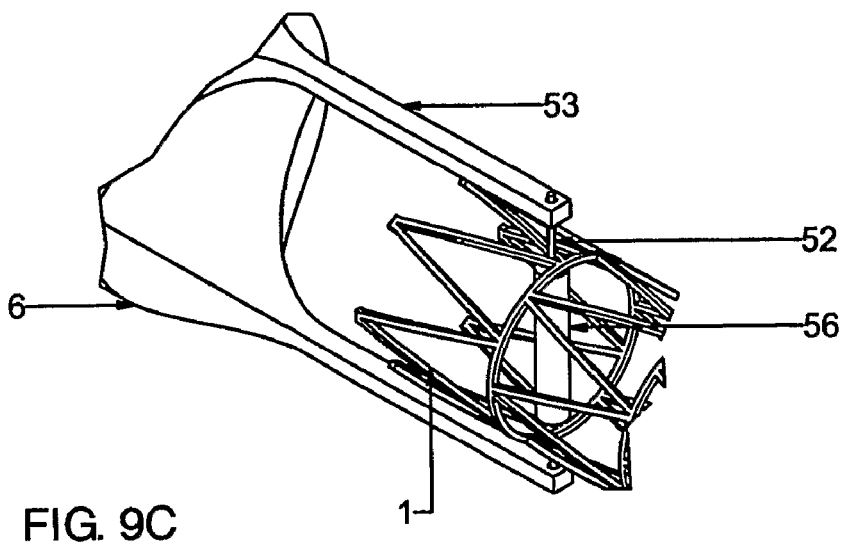
FIG. 9C is an isometric view showing an alternative support member to contact a stent having one centering element.

Another exemplary support member designed to prevent coating defects by minimizing the area contacting the stent is illustrated in FIG. 9A, FIG. 9B and FIG. 9C. Referring to FIG. 9A, the support member includes a structure 53 at least partially surrounding one end of the stent 1, and member 52 that is connected to the structure 53 at both ends and contacts the stent. The member 52 may consist of a rod or a thread and the like. To facilitate cleaning or replacement of the portion of the support member contacting the stent, the member is preferably detachably mounted to the structure. The member 52 may be coupled to the structure 53 by means of a clamping mechanism to facilitate mounting and to secure the member 52. Alternatively, the member can be part of the structure. As shown in FIG. 9B and FIG. 9C, the member 52 may furthermore comprise at least one portion having a larger cross-section to center the stent. Referring to FIG. 9B, two spheres 55 may be provided to contact the inner surface of the stent. The spheres are preferably located equidistant from the longitudinal center axis of the support member to align the stent in relation to the support member. With reference to FIG. 9C, a rod 56 is provided to contact the inner surface of the stent. The ends of the rod are located equidistant from the longitudinal center axis of the support member to align the stent in relation to the support member. Thus, a run out of the stent is prevented by precisely aligning the stent axis in relation to the rotation axis.

Figure 10:
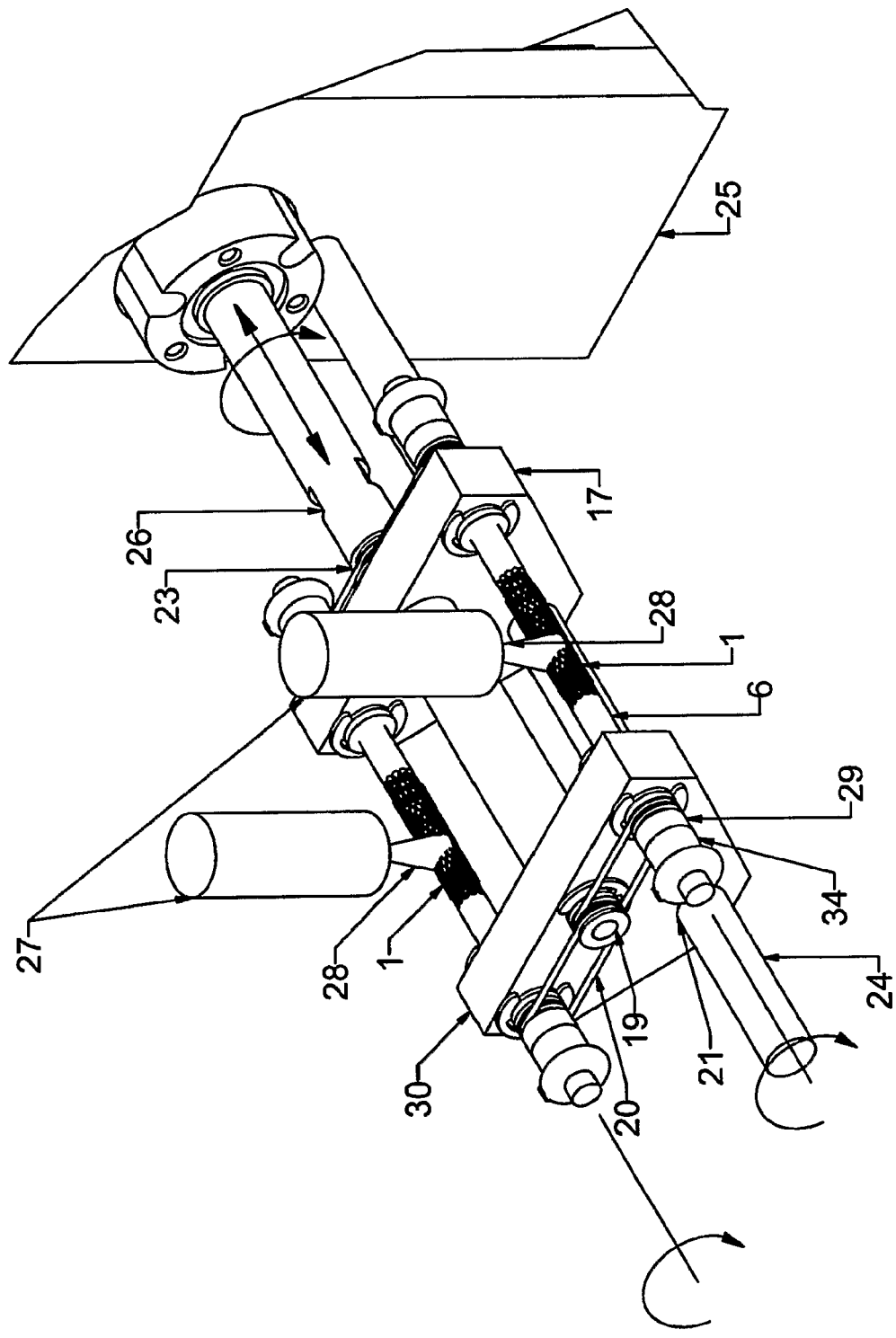
FIG. 10 is an isometric view showing an apparatus comprising a holding device to support and to rotate two stents during a spray coating process.

FIG. 10 shows an exemplary stent holding apparatus and spray coating setup. For increased production output, the apparatus can be equipped with a larger frame to accommodate twelve support members to secure up to six stents. Its compact design allows the integration of two apparatuses in an isolator to coat twelve stents simultaneously. The holding device 30, shown in detail in FIG. 4A, is detachably connected via coupling 23 to the drive shaft 26 of a motion unit 25 and mounted to guide member 24 at guide section 21. It is aligned via guide sections 21 in relation to the guide member 24. The longitudinal axis of the guide member 24 is preferably parallel to the longitudinal axis of the drive shaft 26 in order to align the holding device in relation to the motion unit 25. The guide section 21 of the holding device 30 is connected to guide member 24 to secure the angular position of the holding device during rotation of the stents and to secure the holding device against revolving. The support members 6 are connected via shaft 19 to drive shaft 26 of motion unit 25. To easily connect shaft 19 to drive shaft 26, the drive shaft may be equipped with an automated clamping mechanism 23. The support members 6 are engaged with the stent at two opposing sides and the stent is securely held and can be rotated in relation to the frame 17. Stop members 34 are coupled to the sleeves 29 to secure the stent.

Rotational and translational movement is transmitted from the drive shaft 26 of motion unit 25 via coupling 23 to the shaft 19 of the holding device 30. Rotational movement is transmitted to the stents 1 via shaft 19, belts 20, sleeves 29, couplings 35, stop members 34, and support members 6. The drive shaft translates the holding device 30 along the guide member 24 to move the stents 1 in a linear direction.

Alternatively, rotary motion can be transmitted from the motion unit to the support member and linear motion is transferred to the frame. In another embodiment, each support member may be connected to a dedicated motion unit that transmits linear and/or rotary motion to the stent.

Two atomizers 27 are provided to apply a coating composition to both stents at the same time. During the application of the coating, the holding device 30 is moved in a linear direction relative to the two atomizers 27 generating spray plume 28, and the stents are rotated. The center axis of the spray plume 28 is preferably perpendicular to the rotation axis of the stents 1 and both axes are located on the same plane. After application of the coating, the holding device can be removed from the drive shaft 26 and guide member 24 to continue, for example, with further process steps like drying and inspection.

By using the holding device of the present invention it is not required to dismount and remount the stents. Thus, damage of the medical devices during handling and inspection can be prevented resulting in savings in time and cost. As shown in the exemplary inspection setup of FIG. 11, the stent holding device 30 is connected to guide members 24, which is coupled to a linear stage 33. The stent 1 can be moved in the x-axis direction along guide members 24 and in the y-axis direction along linear stage 33 to position the stent in relation to a measurement and/or inspection apparatus. By turning the shaft 19 of the holding device along its c-axis, the stent 1 is rotated and the coating is inspected using a microscope 32.

Figure 11:
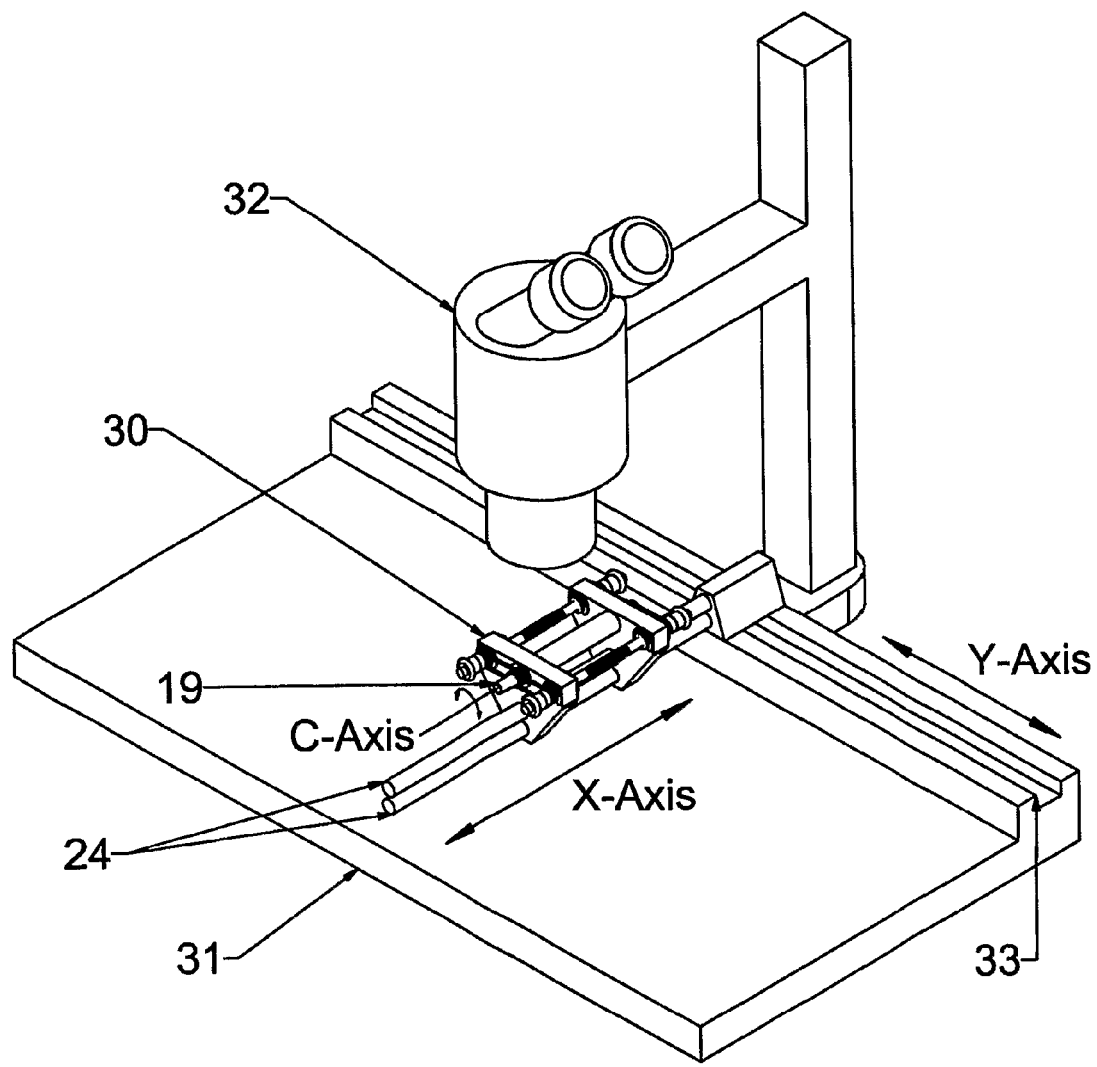
FIG. 11 is an isometric view showing a holding device to support and to rotate two stents during the step of optical inspection.

The following method of precisely aligning and transmitting rotary and/or linear motion to one or more stents using the apparatus of the present invention is being provided by way of illustration and is not intended to limit the embodiments of the present invention. Referring back to FIG. 10, the stents 1 are mounted, and engaged with the support members 6. The axial position of the support members 6 is secured by connecting the stop members 34 to the sleeves 29. To check proper mounting of the stents the shaft 19 may be manually rotated. In another step, the holding device 30 with loaded stents 1 is placed on the guide member 24. The holding device is slid along guide member 24 and is moved towards and connected to the drive shaft 26 of motion unit 25. Rotary motion is transmitted from the drive shaft 26 via shaft 19, belts 20, sleeves 29, and stop members 34 to the support members 6, and the stents 1 are rotated about their longitudinal axis. To move the holding assembly along the guide member 24 in relation to the atomizers 27, linear motion is transmitted from the motion unit 25. A coating can be applied by spraying a coating composition using the atomizers 27. After application of the coating, the shaft 19 is disconnected from the drive shaft 26 of motion unit 25 and the holding device is removed from the guide member 24. The stents may remain mounted on the holding device to allow drying of the coating and subsequent inspection. One skilled in the art can appreciate that drying may be accomplished in a variety of ways based on the coating formulation used. To inspect the coating, the stent holding device 30 may be placed with mounted stent 1 on an inspection table 31, as shown in FIG. 11, and may be moved along the x-axis and/or y-axis to align the stent in relation to microscope 32. The stent may be rotated about its longitudinal axis by turning the shaft of the stent holding device along its c-axis.

STENT COATING EXAMPLE

The following example is being provided by way of illustration and is not intended to limit the embodiments of the present invention.

Stents (manufactured by STI, Israel) having a diameter of 2 mm and a length of 20 mm may be coated.

The coating composition may include a non-bioabsorbable or bioabsorbable polymer, a solvent capable of dissolving the polymer at the concentration desired in the composition, and a therapeutic substance.

The coating composition may comprise a solvent, a polymer, and a therapeutic substance. The therapeutic substance may include, but is not limited to, proteins, hormones, vitamins, antioxidants, antimetabolite agents, anti-inflammatory agents, anti-restenosis agents, anti-thrombogenic agents, antibiotics, anti-platelet agents, anti-clotting agents, chelating agents, or antibodies. Examples of suitable polymers include, but are not limited to, synthetic polymers including polyethylen (PE), poly(ethylene terephthalate), polyalkylene terepthalates such as poly(ethylene terephthalate) (PET), polycarbonates (PC), polyvinyl halides such as poly(vinyl chloride) (PVC), polyamides (PA), poly(tetrafluoroethylene) (PTFE), poly(methyl methacrylate) (PMMA), polysiloxanes, and poly(vinylidene fluoride) (PVDF); biodegradable polymers such as poly(glycolide) (PGA), poly(lactide) (PLA) and poly(anhydrides); or natural polymers including polysaccharides, cellulose and proteins such as albumin and collagen. The coating composition can also comprise active agents, radiopaque elements or radioactive isotopes. The solvent is selected based on its biocompatibility as well as the solubility of the polymer. Aqueous solvents can be used to dissolve water-soluble polymers, such as Poly(ethylene glycol) (PEG) and organic solvents may be used to dissolve hydrophobic and some hydrophilic polymers. Examples of suitable solvents include methylene chloride, ethyl acetate, ethanol, methanol, dimethyl formamide (DMF), acetone, acetonitrile, tetrahydrofuran (THF), acetic acid, dimethyle sulfoxide (DMSO), toluene, benzene, acids, butanone, water, hexane, and chloroform. For the sake of brevity, the term solvent is used to refer to any fluid dispersion medium whether a solvent of a solution or the fluid base of a suspension, as the invention is applicable in both cases.

The stents may be mounted on the holding device of the present invention as illustrated in FIG. 4A. Two air-assisted external mixing atomizers can be used to disintegrate the coating composition into fine droplets and apply the coating to the stents. Alternatively, ultrasonic nozzles, or dispensers can also be employed for the application of the composition.

The holding device may move in a linear direction along the guide member in relation to the atomizers and may rotate both stents simultaneously at the same angular velocity. The two spray nozzles can disintegrate the coating solution into fine droplets at a liquid flow rate of about 0.1 to 80 ml/h and an atomizing pressure ranging from about 0.3 to about 1.5 bar. In order to achieve a fine atomization, the nozzles are preferably operated at an atomizing gas flow rate of 5 l/min and at an atomizing pressure of 0.8 bar. The nozzles generate droplets having a volumetric median diameter between approximately 2 and 7 microns and a largest droplet diameter of less than 20 microns. For best results, the spray axis of the atomizer is preferably perpendicular to the rotation axis of the stent and both axes are in the same plane. The spray nozzles may be positioned at a distance of approximately 12 to 35 mm from the nozzle tip to the outer surface of the stent.

A syringe pump, which is operated at a constant flow rate, can be used to feed the coating substance to the atomizer. The flow rate of the coating solution may range from about 1 to 50 ml/h and is preferably 5 ml/h During the application of the coating solution, rotary motion is transmitted from the drive shaft of the motion unit to the stents to rotate the stents about their central longitudinal axes. The rotation speed can be from about 5 to about 250 rpm. By way of example, the stent may rotate at 130 rpm. The stents are translated along their central longitudinal axes along the atomizers. The translation speed of the stents can be from about 0.2 to 8 mm/s. When applying the coating solution, the translation speed is preferably 0.5 mm/s. The stents can be moved along the atomizer one time to apply the coating in one pass or several times to apply the coating in several passes. Alternatively, the atomizer may be moved one time or several times along the stent length.

Figure 12:
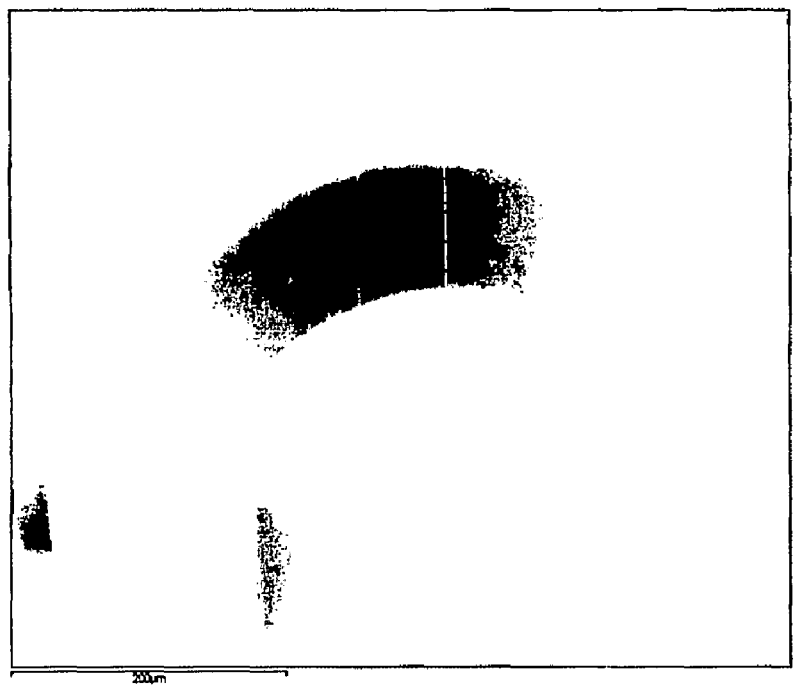
FIG. 12 is an image of a portion of a coated stent.
Figure 13:
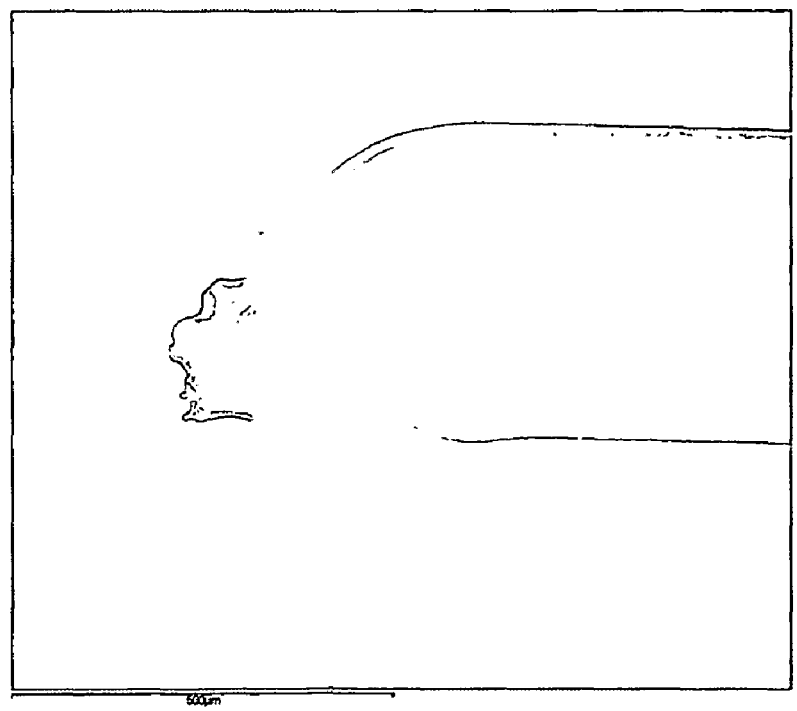
FIG. 13 is an image of a portion of a coated stent comprising a coating defect.

Coating trials of several stents were performed. FIG. 12 shows a portion of a stent coated using the holding device of the present invention. The number of coating defects, especially at the ends of the stents, was reduced by using the holding device of the present invention.

While the invention will be described in connection with certain embodiments, it will be understood that the invention is not limited to these embodiments. On the contrary, the invention includes all alternatives, modifications and equivalents as may be included within the spirit and scope of the present invention. Details in the Specification and Drawings are provided to understand the inventive principles and embodiments described herein, to the extent that would be needed by one skilled in the art to implement those principles and embodiments in particular applications that are covered by the scope of the claim.

The invention claimed is:

1. A holding device for handling, securing and rotating at least one stent, comprising:
a frame; and
at least two support members being coupled to the frame and in contact with at least a portion of the stent,
wherein the frame connects the support members and surrounds at least partially the stent while not extending through the stent;
the support members do not extend completely through the stent and are rotably mounted to the frame to rotate the stent;
the support members have a first position of being engaged with the stent at two opposing sides to secure the stent and the support members can be rotated in relation to the frame to rotate the stent;
at least one support member has a second position of being disengaged from the stent to unload the stent;
and the support members can remain coupled to the frame during unloading of the stent.

2. The holding device according to claim 1, further comprising at least one shaft, which can be rotated in relation to the frame in order to transmit rotary motion to the support members.

3. The holding device according to claim 2, further comprising members to transmit rotary motion between the shaft and the support members.

4. The holding device according to claim 1, additionally comprising sleeves being rotably mounted to the frame, wherein in the first position the support member is coupled to the sleeve to transmit rotary motion and in the second position the support member is uncoupled from the sleeve.

5. The holding device according to claim 1, wherein the support member comprises a structure partially surrounding one end of the stent and a member connecting the surrounding portion of the structure in order to contact the stent.

6. The holding device according to claim 5, wherein the member is part of the structure.

7. The holding device according to claim 5, wherein the member is exchangeable.

8. The holding device according to claim 5, wherein the member comprises at least one portion having a larger cross-section to center the stent.

9. The holding device according to claim 8, wherein the portion has a spherical shape.

10. The holding device according to claim 8, wherein the portion has a cylindrical shape.

11. A holding device for handling, securing and rotating at least one stent, comprising:
a frame: and
at least two support members being coupled to the frame and in contact with at least portion of the stent, the support members have a first position of being engaged with the stent at two opposing sides to secure the stent and the support members can be rotated in relation to the frame to rotate the stent; and
at least one support member has a second position of being disengaged from the stent to unload the stent, wherein the support members contacts at least partially the inner surface of the stent and the portion of the support member contacting the inner surface of the stent comprises at least two sides being parallel to the longitudinal axis of the stent.

12. A holding device for handling, securing and rotating at least one stent, comprising:

a frame; and at least two support members being coupled to the frame and in contact with at least a portion of the stent, the support members have a first position of being engaged with the stent at two opposing sides to secure the stent and can be rotated in relation to the frame to rotate the stent; and at least one support member has a second position of being disengaged from the stent to unload the stent, wherein the support member contacts at least partially the inner surface of the stent and the portion of the support member contacting the inner surface of the stent comprises at least two edges being parallel to the longitudinal axis of the stent.

13. A method for securing and applying rotary motion to at least one stent using a holding device including a frame surrounding at least partially the stent while not extending through the stent and accommodating at least two support members being coaxially arranged, coupled to the frame, not extending completely through the stent and rotable in relation to the frame, comprising the steps of:

placing at least one support member at a first position in which the distance between the support members is larger than the stent length;

placing a stent between the support members wherein the support members remain coupled to the frame during said placing of said stent between the support members;

placing at least one support member at a second position in which the support members secure the stent; and transmitting rotary motion to the support members to rotate the stent in relation to the frame.

14. The method according to claim 13, wherein a shaft is rotably mounted to the frame of the holding device is additionally provided and rotary motion is induced at the shaft and transmitted to the support members to rotate the stent in relation to the frame.

15. The method according to claim 13, further comprising the step of applying a coating to the stent.

16. The method according to claim 13, further comprising the step of positioning the holding device so that at least one portion of the holding device is in contact with at least one guide member.

17. The method according to claim 16, further comprising the step of translating the holding device along the guide member.

18. The holding device according to claim 1, wherein the holding device is part of an apparatus for applying linear and rotary motion to at least one stent, comprising:

at least one guide member; and a detachable holding device having a frame, at least one shaft being rotable in relation to the frame, and at least two support members being rotable in relation to the frame and securing a stent at two opposing ends, wherein the holding device is in contact with at least a portion of the guide member to secure its angular position and can be moved along the guide member to translate the stent; and the stent can be rotated in relation to the holding device by applying rotary motion to at least one of the rotable members being coupled to the frame.

19. The apparatus according to claim 18, further comprising a spray source to apply a coating to the stent.

20. The apparatus according to claim 18, additionally comprising at least one inspection device, wherein the holding device can be moved along at least one guide member to position the stent in relation to the inspection device.

* * * * *